United States Patent [19]

Häusler

[11] 4,311,147

[45] Jan. 19, 1982

[54] APPARATUS FOR CONTACT-FREE DISINTEGRATION OF KIDNEY STONES OR OTHER CALCULI

[75] Inventor: Eberhard Häusler, Saarbrücken, Fed. Rep. of Germany

[73] Assignee: Richard Wolf GmbH, Knittlengen, Fed. Rep. of Germany

[21] Appl. No.: 147,955

[22] Filed: May 8, 1980

[30] Foreign Application Priority Data

May 26, 1979 [DE] Fed. Rep. of Germany ....... 2921444
May 26, 1979 [DE] Fed. Rep. of Germany ....... 7915289

[51] Int. Cl.[3] .......................................... A61B 17/22
[52] U.S. Cl. .......................................... 128/328
[58] Field of Search .......................... 128/328, 24 A

[56] References Cited

U.S. PATENT DOCUMENTS 3,237,623 3/1966 Gordon ........................ 128/24 A
3,785,382 1/1974 Kloiber et al. .................. 128/328
3,942,531 3/1976 Hoff et al. ...................... 128/328
4,094,306 6/1978 Kossoff ...................... 128/24 A X

FOREIGN PATENT DOCUMENTS 2650624 5/1978 Fed. Rep. of Germany ...... 128/328

*Primary Examiner*—Lee S. Cohen
*Attorney, Agent, or Firm*—Kinzer, Plyer, Dorn & McEachran

[57] ABSTRACT

This invention relates to apparatus for contact-free disintegration of kidney stones or other calculi of the kind in which electrical discharges are generated across an under water spark gap in the focus line of an elliptical reflector having annular or spiral surfaces. The calculus which is to be disintegrated is located into the focus of the reflector and in accordance with invention electrode elements are positioned at intervals in the focus line of this reflector on an insulating carrier. The latter is provided with high tension connectors at its ends and the electrode elements are arranged to form consecutive individual spark gaps.

The gaps between the electrode elements may be of constant dimensions or may vary so as to produce variations in pressure distributed at a focus point if so desired.

3 Claims, 3 Drawing Figures

FIG. 1
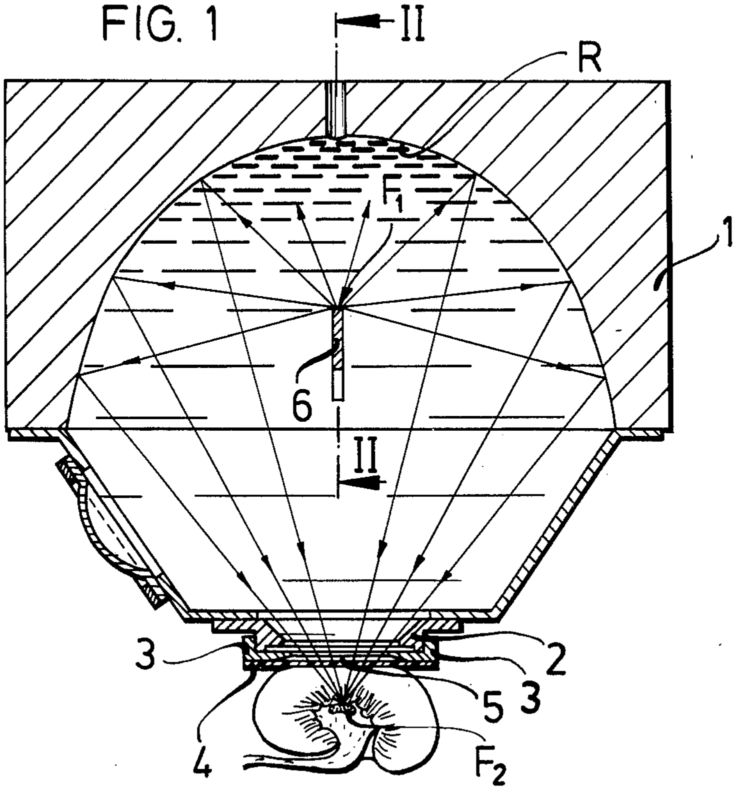
FIG. 3
FIG. 2
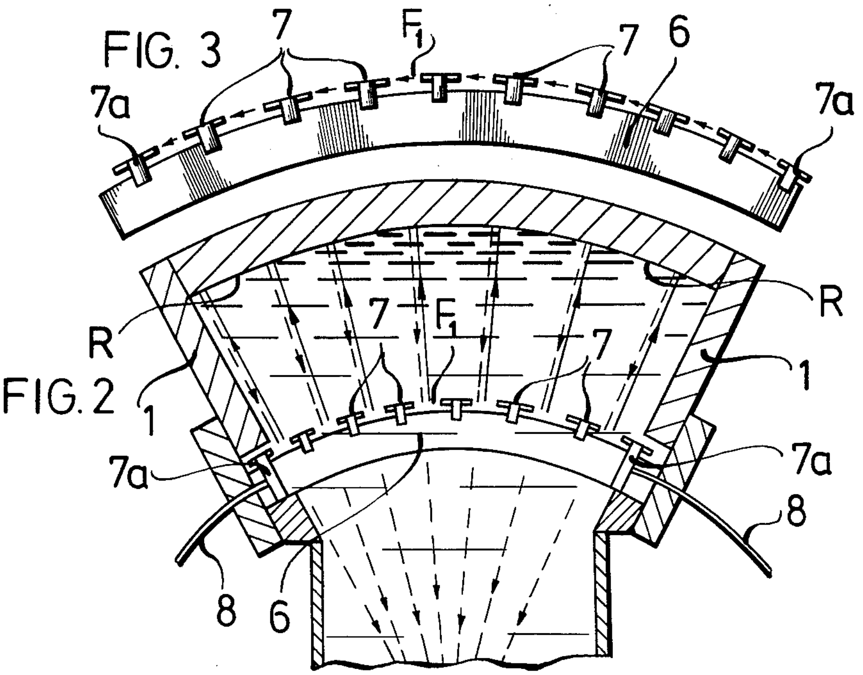

APPARATUS FOR CONTACT-FREE DISINTEGRATION OF KIDNEY STONES OR OTHER CALCULI

BACKGROUND OF THE INVENTION

The present invention relates to a device for contact-free disintegration of kidney stones or other calculi, of the kind in which means are provided to generate discharges across an underwater spark gap in the focus line of an elliptical reflector having annular or spiral surfaces, into whose focus the calculus which is to be disintegrated is located. Hereinafter, such apparatus will be referred to as "of the kind described".

Apparatus for generating hydraulic shock waves is already known in which a copper wire is stretched over an insulating bracket in the focal point line of an elliptical annular surface reflector or torus reflector and this copper wire is vapourised throughout the length of the supporting bracket upon being connected to a source of high voltage and by virtue of the gas discharge formed generated the hydraulic shock wave, for the purpose of generating a shock wave under water. The wire must be pulled over the bracket again in each case to generate the following shock waves, and this requires considerable expenditure of time by the doctor. With this apparatus therefore, it is not possible, if at all, easily to generate shock waves following each other at short intervals.

It is an object of the invention to provide apparatus for generating a plurality or series of underwater discharges at the same time in the focal point line of the reflector, without special operations being needed for this purpose.

SUMMARY OF THE INVENTION

In apparatus of the kind described, the invention consists in that electrode elements are positioned at intervals in the focus line of said reflector on an insulating carrier equipped with high tension connectors at the extremities and said electrode elements are arranged to form consecutive individual spark gaps.

It is thus necessary merely to connect the electrodes at the extremities of the row of electrode elements to the source of high voltage, so that discharges are thereupon generated simultaneously between every two such consecutive elements and a series of spherical shock waves then operates simultaneously on a kidney stone or other calculus situated at the focus for its disintegration. The features of the invention may be applied in all reflectors having a focal line, with which is coordinated a focal point which is to be placed in coincidence with the position of the stone which is to be disintegrated.

BRIEF DESCRIPTION OF THE DRAWINGS

In order that the invention may be more clearly understood, reference will now be made to the accompanying drawings which show one embodiment thereof by way of example and in which:

FIG. 1 shows an embodiment of the invention for generating hydraulic shock waves for disintegration of a kidney stone, in cross-section, FIG. 2 shows a cross-section through the reflector along the line II—II of FIG. 1, and FIG. 3 shows a sideview of a carrier comprising electrode elements following each other at intervals.

DETAILED DESCRIPTION OF PREFERRED EMBODIMENTS

Referring now to the drawings, according to FIG. 1, a device for electrical pulse discharge, particularly for generating hydraulic shock waves, is incorporated in a housing 1 filled with water. The housing 1 is delimited at its upper portion by an elliptical annular surface reflector R opposite which is located a metal diaphragm 2 delimiting the housing at its lower portion and situated in a mounting 3. Since the diaphragm 2 does not exactly fit the contours of the body of the patient, the mounting 3 has connected to it below the diaphragm 2 a resilient diaphragm 4 which between itself and the diaphragm 2 encloses an intermediate space 5 filled with water or with a fluid which has an acoustic impedance similar to that of the organ itself. This resilient diaphragm 4 may be formed as a deformable envelope or a bag which adapts itself perfectly to the kidney or the body of the patient and thereby offers its deformability an opportunity of adjusting the second focal point F2 of the elliptical annular surface reflector R precisely on the stone or other calculus which is to be disintegrated, as described for example in German patent application No. p2913251.2.

Elliptical annular surface reflectors or alternatively elliptical spiral surface reflectors having one or one and a half turns, have a curved focal line F1. In this line is installed an arcuate insulating carrier 6 which, along its length carries a series of individual electrode elements 7, the gaps between which are of equal or unequal lengths. Any two consecutive elements form an individual spark gap when the elements are connected to high voltage. Connectors 8 or a surge voltage generator are connected to electrodes 7*a* situated at the extremities of the carrier. Upon switching on the surge voltage, a pulse-like discharge occurs simultaneously at the individual spark gaps, thereby simultaneously generating hydraulic shock waves which cause disintegration of a kidney stone or like calculus. The phase surfaces of the individual spark gaps are spherical. The contour of these phase surfaces forms a curved cylindrical wavefront the axis of which is given by the focal line of the reflector. For extensive approximation of the curved linear source it is necessary to install as many separate spark gaps as possible on the bracket. To effect the pressure distribution at the focal point, it may be advantageous to select the spacing of the individual spark gaps to be irregular, that is greater at the centre than in the marginal portion or vice versa. Consequently, it is no longer necessary after each separate previous discharge to replace the vapourised wire by external manipulation, e.g. by infeed of the wire by means of special operations.

It will be apparent that it is possible to replace the arcuate carrier 6 carrying the consecutive electrode elements 7 with a new carrier complete with new electrode elements after simple withdrawal from the housing, for the next stone disintegration.

I claim:

1. In apparatus for contact-free shock wave disintegration of kidney stones or other calculi by generating electrical discharges across an underwater spark gap in the focus line of an elliptical reflector having two foci, namely, a first and second focus, and into whose second focus the calculus which is to be disintegrated is to be located, the improvement which consists in that plural electrode elements are positioned at intervals along the first focus of said reflector, said electrode elements being supported on an insulating carrier equipped with high tension connectors at the extremities, said connectors being electrically associated with the electrode elements, and said electrode elements being so spaced from one another as to form consecutive individual spark gaps.

2. Apparatus according to claim 1, wherein the gaps between said electrode elements are of constant dimensions.

3. Apparatus according to claim 1, wherein the gaps between said electrode elements vary as to dimension.

* * * * *